United States Patent
Thuramalla et al.

(10) Patent No.: US 8,273,048 B2
(45) Date of Patent: Sep. 25, 2012

(54) SYSTEM AND METHOD FOR DIVERTING FLOW TO FACILITATE MEASUREMENT OF SYSTEM PARAMETERS

(75) Inventors: Naveen Thuramalla, Ithaca, NY (US); Nikolai Krivitski, Ithaca, NY (US); Mark Alsberge, Marathon, NY (US)

(73) Assignee: Transonic Systems, Inc., Ithaca, NY (US)

( * ) Notice: Subject to any disclaimer, the term of this patent is extended or adjusted under 35 U.S.C. 154(b) by 833 days.

(21) Appl. No.: 12/082,692

(22) Filed: Apr. 11, 2008

(65) Prior Publication Data

US 2008/0275354 A1 Nov. 6, 2008

Related U.S. Application Data

(60) Provisional application No. 60/922,863, filed on Apr. 11, 2007, provisional application No. 60/962,554, filed on Jul. 30, 2007.

(51) Int. Cl.
*A61M 37/00* (2006.01)
(52) U.S. Cl. .................... 604/4.01; 600/300
(58) Field of Classification Search .......... 600/300, 600/322, 326, 364, 368, 454, 465, 468, 504; 604/4.01–6.16, 7–9, 506–508, 19, 27, 48; 422/44, 99, 101; 210/644
See application file for complete search history.

(56) References Cited

U.S. PATENT DOCUMENTS

| | | | | |
|---|---|---|---|---|
| 5,690,831 A * | 11/1997 | Kenley et al. | ................. | 210/646 |
| 6,158,458 A * | 12/2000 | Ryan | ......................... | 137/515.5 |
| 6,208,880 B1 | 3/2001 | Bentsen et al. | | |
| 7,691,046 B2 * | 4/2010 | Sullivan | ........................ | 600/16 |
| 2004/0158133 A1 | 8/2004 | Krivitski et al. | | |
| 2008/0175719 A1 * | 7/2008 | Tracey et al. | ................... | 417/38 |

OTHER PUBLICATIONS

PCT—Notification of Transmittal of the International Search Report and the Written Opinion of the International Searching Authority, or the Declaration, dated Nov. 26, 2008.
PCT—International Search Report, dated Nov. 26, 2008 (6 pages).
PCT—Written Opinion of the International Searching Authority, dated Nov. 26, 2008 (5 pages).

* cited by examiner

*Primary Examiner* — Tatyana Zalukaeva
*Assistant Examiner* — Benedict L Hanrahan
(74) *Attorney, Agent, or Firm* — Brian B. Shaw; Harter Secrest & Emery LLP

(57) ABSTRACT

A method and various devices are disclosed that facilitates the measurement of hemodynamic parameters by injection of an indicator in an indicator dilution technique using an extracorporeal circuit connected to a patient. Specifically, the invention deals with problems caused by the spike in pressure in an extracorporeal line that result from the injection of a bolus. The method and various devices provide for diversion of blood during an indictor injection process and then return of the diverted blood back into the system after the injection is completed. The variations of the invention use diversion lines, accommodating cases and other devices that are designed to accumulate blood displaced during injection and then returning the blood to the extracorporeal circuit after injection.

16 Claims, 10 Drawing Sheets

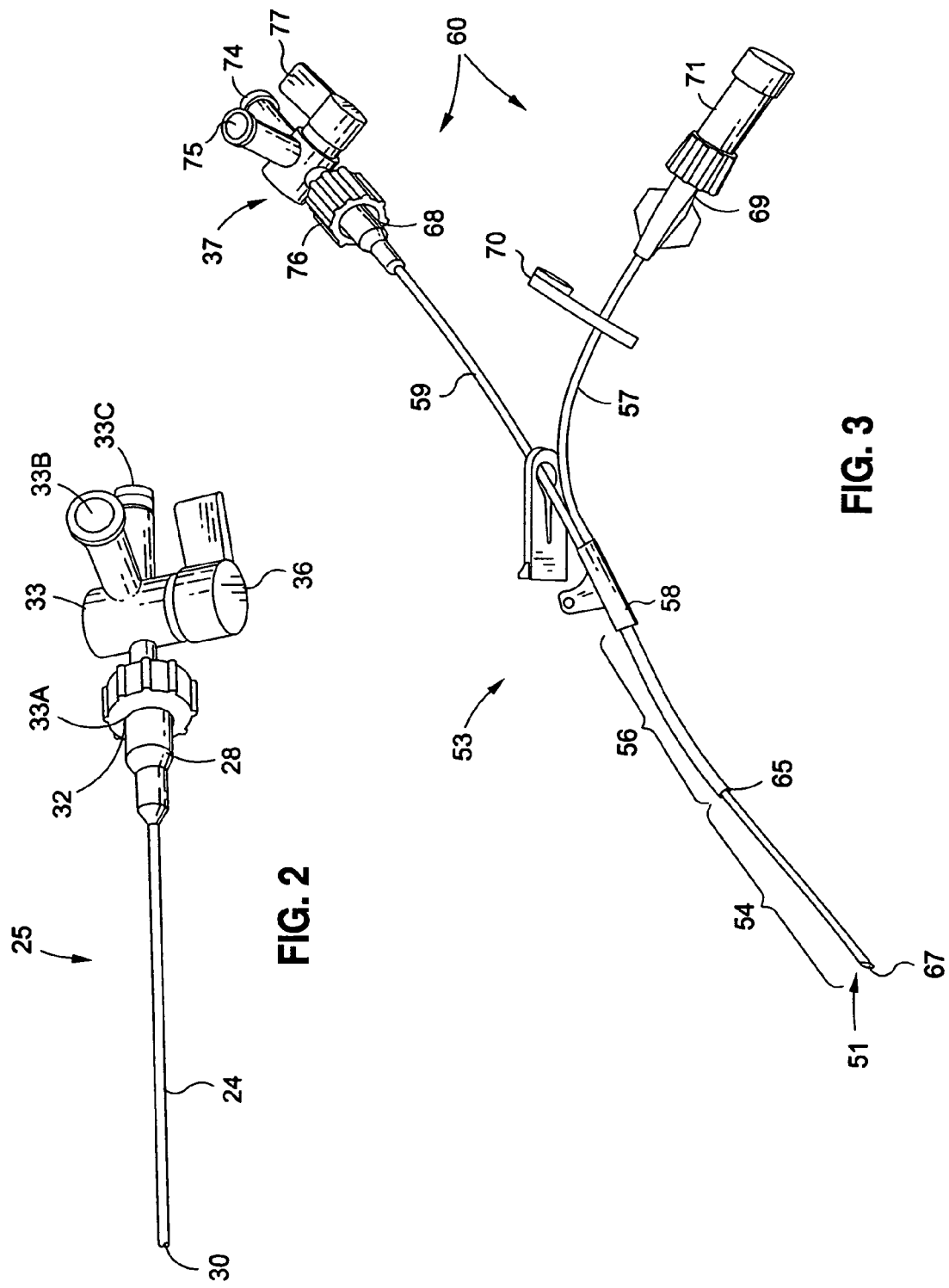

US 8,273,048 B2

SYSTEM AND METHOD FOR DIVERTING FLOW TO FACILITATE MEASUREMENT OF SYSTEM PARAMETERS

CROSS-REFERENCE TO RELATED APPLICATIONS

The present application claims priority under 35 USC §119(e) from U.S. provisional application Ser. No. 60/922,863 filed on Apr. 11, 2007 titled System and Method for Redirecting Flow to Facilitate Measurement of System Parameters and U.S. provisional application Ser. No. 60/962,554 filed Jul. 30, 2007 and titled System and Method for Redirecting Flow to Facilitate Measurement of System Parameters.

STATEMENT REGARDING FEDERALLY SPONSORED RESEARCH OR DEVELOPMENT

Not applicable.

REFERENCE TO A "SEQUENCE LISTING"

Not applicable.

FIELD OF THE INVENTION

The present invention relates to a system and method for facilitating the determination of the physical parameters of a dynamic fluid system. More particularly it relates to a method for diverting flow during an indicator dilution procedure in an extracorporeal circulatory system to facilitate determination of various hemodynamic parameters.

BACKGROUND OF THE INVENTION

Indicator dilution techniques have been used for well over a hundred years to determine various hemodynamic parameter, in particular blood flow volume etc. Indicator dilution involves the injection of some type of indicator into the circulatory system of the patient as part of the process of using the technique. For example two common types of indicators that can be injected into a circulatory system are saline solutions and dye solutions. Flow is determined by the concentration of the indicator after the indicator has flown through the system being studied. It should be noted that those skilled in the art are familiar with many other types of indicators including thermal dilution and many different techniques and sensors for implementing indicator dilution measurements.

Quite often indicator dilution is used with an extracorporeal circulating line which is attached to a patient to determine blood flow, cardiac output, blood water content or other hemodynamic parameters of the patient. An example of an extracorporeal line established in a patient for determination of cardiac output and other hemodynamic parameters is disclosed in pending U.S. patent application Ser. No. 11/370,721 filed Mar. 7, 2006 and titled System and Method for Determining Cardiac Blood Flow, which application is incorporated herein by reference as if set forth herein at length. Briefly, this patent application discloses an extracorporeal circuit that connects to the ends of a standard patient arterial catheter and venous catheter to allow the circulation of blood from the patient through the extracorporeal circuit and back into the patient. The purpose as described in detail in that patent application is to measure cardiac output and other blood parameters with indicator dilution techniques.

The use of indicator dilution techniques with extracorporeal circuits, in particular the bolus or sudden injection method of indicator dilution, can provide highly accurate readings of blood flow volume, cardiac output, etc. However, the sudden injection of the bolus of indicator creates problems and in fact can cause havoc to the flow of blood in the extracorporeal circuit. The sudden injection into an extracorporeal blood circuit of a bolus of indicator, such as a saline solution, tends to disrupt the ordinary flow of blood in the extracorporeal blood circuit in that portion of the circuit upstream from the site of injection. Typically, the indicator is being injected into an extracorporeal blood line that is already carrying its full capacity of blood flow. The sudden injection thus causes a spike in the pressure in the extracorporeal blood circuit at the point of injection as it is being forced into the line.

This sudden spike in pressure and interruption in flow of blood in the extracorporeal circuit typically results in a stoppage the flow of blood in the extracorporeal circuit upstream from the site of injection and quite often can cause a reversal of the flow of blood. This sudden stoppage or reversal of flow, even though it is only for the period of injection, creates problems with the final readings obtained by the indicator dilution technique. These problems can arise in passive systems where there is no pump or other device to regulate flow. These problems are also significant problems in systems where the blood flow in the extracorporeal circuit has been induced by and is being regulated by a pump. The stoppage of flow and/or its reversal upstream from the site of injection causes a corresponding slowing down or stopping of a pump located upstream from the injection site. The slowing or stopping of the pump introduces inaccuracies into the readings ultimately obtained with the indicator dilution injection.

Thus what is needed is a system and method that allows for the injection of a bolus into an extracorporeal circuit that prevents the sudden spike in pressure in the extracorporeal circuit from disrupting the flow of blood in the extracorporeal circuit. A system and method that eliminates the possibility that blood flow in the extracorporeal circuit above the site of injection will stop or reverse. A system and method that thus prevents conditions from developing in the extracorporeal circuit that interfere with a pump regulating flow of blood in the extracorporeal circuit.

SUMMARY

Thus, it is an objective of the present invention to provide a system and method for injecting a bolus of indicator that prevents the spike in pressure caused by the injection from disrupting the flow of blood in the extracorporeal circuit. It is a further objective to provide a system and method that maintains continuous blood flow in an extracorporeal circuit and avoids stoppage or reversal of blood flow during injection of a bolus in the extracorporeal circuit. It is an additional objective of the present invention to provide a system and method that prevents a pump regulating flow in the extracorporeal circuit from being slowed or stopped during injection of a bolus of indicator.

To achieve these and other objectives the invention provides a method for facilitating the injection of a bolus into an extracorporeal circuit that has the steps of: a.) diverting a flow blood in an extracorporeal circuit above an injection site of a bolus during the injection of the bolus into the extracorporeal circuit; and b) reintroducing the blood flow into the extracorporeal circuit that had been diverted during the injection of the bolus after the injection of the bolus has stopped. In this method the steps of diverting blood and then reintroducing it can be accomplished by providing a second blood line for redirecting flow of diverted blood from a point upstream in the extracorporeal circuit from the injection site in the extracorporeal circuit around the injection site to a point downstream from the injection site in the extracorporeal circuit. In another aspect of this method the step of diverting blood and then reintroducing it can be accomplished by diverting the blood upstream from the injection site into a volume accumulating reservoir connected to the extracorporeal circuit, which reservoir is located upstream from the injection site in the extracorporeal circuit and then reintroducing the blood from the volume accumulating reservoir into the extracorporeal circuit after the injection ceases. In a further aspect of the method of the invention it includes the step of blocking flow between the injection site and diverting site during the injecting step.

In a further aspect of the invention it provides a flow diversion apparatus in fluid communication with an extracorporeal circuit at a point upstream from an injection site in the extracorporeal circuit, the flow diversion apparatus diverting blood flow upstream in the extracorporeal circuit when a bolus is injected and reintroduces the diverted blood flow into the extracorporeal circuit after diversion of the blood stops. The flow diversion apparatus for diverting blood during injection and returning the diverted blood after injection can be selected from one of the following devices: a flow volume accommodating case, an automatic flow pressure relief system, a diverting lumen providing an alternate route to a venous catheter, or a syringe connected to the extracorporeal circuit for manually diverting blood and then returning the diverted blood to the extracorporeal circuit. In a further aspect of this variation of the invention it includes a check valve positioned between the flow diversion apparatus and the injection site to prevent flow downstream from the check valve during injection of an indicator.

In another aspect of the invention it provides a device for relieving excess pressure in an extracorporeal circuit during and injection process the device having a) a case connectable to an extracorporeal circuit; b) a conduit through the case for unimpeded flow of blood through the conduit and thus through the case, the conduit forming part of the extracorporeal circuit; c) the conduit has an expansion portion responsive to pressure increases in blood flowing in the conduit such that the expansion portion accommodates a build up of blood caused by a constriction or interruption of flow downstream from the case in the extracorporeal circuit; and d) wherein the expansion chamber accommodates the build up of blood by expansion of the expansion portion into a volume accumulation reservoir chamber within the case without loss of blood and upon the ending of the constriction or interruption of flow the expansion portion contracts back to its original shape returning the accumulated blood back to the flow of blood in the extracorporeal circuit. In one variation the expansion portion of the device responsive to pressure is rubber like material forming the conduit. In another variation of the invention the expansion portion is a lid forming a portion of the conduit wall adjacent to the expansion chamber which lid is spring loaded to thereby allow it to retract into the expansion chamber in response to restrictions or interruptions of blood flow. In another aspect of the invention the it includes a one way or check valve positioned in the extracorporeal circuit between the site of injection and the case with expansion chamber to prevent both back flow from the site of the injection and stop flow upstream from the one way valve to thereby accumulate blood in the expansion chamber during injection of an indicator.

In another aspect of the invention it provides an apparatus for relieving excess pressure in an extracorporeal circuit during and injection process which apparatus consists of: a) a fluid line connected at a first end to an extracorporeal circuit at a point upstream from an injection site in the extracorporeal circuit; b) a bubble trap connected at a first end of the bubble trap to a second end of the fluid line; c) a saline bag in fluid communication with the bubble trap through a tube that runs from the saline bag to a second end of the bubble trap; d) the saline bag being positioned at a point above the bubble trap and the bubble trap being positioned above the extracorporeal circuit such that fluid will run from the saline bag to the bubble trap to the extracorporeal circuit; e) a clamping mechanism that can be secured on the tube connecting the saline bag and the bubble trap after fluid from the saline bag has filled the fluid line and partially fills the bubble trap to thereby stop flow of fluid from the saline bag and seal off the bubble trap and the fluid line; and f) wherein fluid filling the fluid line and half filing the bubble trap is in a dynamic pressure balance with blood flowing in the extracorporeal circuit at standard pressure and wherein when a restriction or blockage of blood flow occurs in the extracorporeal circuit downstream from the connection of the fluid line blood from the extracorporeal circuit flows into the fluid line and when the restriction or blockage of flow ends the blood in the fluid line flows back into the extracorporeal circuit.

In another aspect of the present invention, the invention achieves these and other objectives by providing: a method for facilitating the determination of hemodynamic parameters which has the steps of: a) establishing a regulated blood flow in an extracorporeal circuit between an arterial connection and a venous connection in a patient; b) diverting blood flow from the extracorporeal circuit; c) injecting an indicator into the extracorporeal circuit; d) accumulating the diverted blood; e) ending injection of the indictor; f) ending diverting of blood from the extracorporeal circuit; g) returning the diverted blood to the extracorporeal circuit; h) measuring the changes caused by the injecting of the indictor; and i) calculating a hemodynamic parameter from the measured change caused by the indicator. In further aspect of this method the step of diverting blood flow consists of diverting blood flow into a second conduit upstream from the indicator injection location, which second conduit diverts flow of the blood around the injection location into a venous connection to the patient. In another aspect of the present invention the steps of diverting blood flow from the extracorporeal circuit, ending diverting of blood from the extracorporeal circuit and returning the diverted blood to the extracorporeal circuit are accomplished by using a pressure activated expansion reservoir.

In another variation of the method of the present invention the steps of diverting blood flow from the extracorporeal circuit, ending diverting of blood from the extracorporeal circuit and returning the diverted blood to the extracorporeal circuit are accomplished by using a pressure activated side fluid line connected to the extracorporeal circuit at a position upstream from the injection site, which side fluid line accepts diverted blood flow from the extracorporeal circuit during the injection step and return diverted blood to the extracorporeal circuit when the injection ends.

In another variation of the present invention it provides a system for facilitating the determination of hemodynamic parameters, which system has: a) an extracorporeal fluid conducting circuit with a first end that connects to an arterial catheter of a patient and a second end connecting to a venous catheter of a patient; b) a fluid propelling apparatus to move fluid through the extracorporeal circuit from the first end to the second end; c) at least one injection port on the extracorporeal circuit for access to the at least one conduit of the extracorporeal circuit; and d) an expandable reservoir in fluid communication with the extracorporeal fluid circuit at a position upstream on the extracorporeal circuit from the injection site for receiving accumulating fluid resulting from a constriction or interruption of flow downstream by an injection of an indicator and then releasing the accumulated fluid to flow down the extracorporeal circuit when the constriction or interruption of flow caused by the injection ceases.

BRIEF DESCRIPTION OF THE DRAWINGS

The invention will be better understood by an examination of the following description, together with the accompanying drawings, in which:

FIG. 2 is a view of a standard arterial catheter;

FIG. 3 is a view of a two lumen venous catheter with which a preferred embodiment of the present invention could be practiced;

DETAILED DESCRIPTION OF THE PREFERRED EMBODIMENT

As noted above the present invention provides a method and system designed to facilitate the use of and indicator dilution technique for the determination of hemodynamic parameters in a circulatory system. Specifically it the invention facilities the injection of indicator. One example of a system and method where the present invention can be used is disclosed in pending U.S. patent application Ser. No. 11/370,721 filed Mar. 7, 2006 and titled System and Method for Determining Cardiac Blood Flow, which application is incorporated herein by reference as if set forth herein at length.

It should be noted that in this specification diverting will be utilized in its ordinary sense and to cover several possibilities to be discussed at length below, such as: 1) redirecting the flow to another location in the extracorporeal circuit or catheter to which the extracorporeal circuit attaches, or 2) accumulating the blood at a particular spot or location upstream from the site of injection where it can then be released to flow down stream. Examples which are set out below of flow redirecting are the second lumen or conduit that directs at lease a portion of the blood flowing in the extracorporeal circuit around the site of injection. Examples set out below of accumulating blood being the volume accumulating case or expansion reservoir, and the flow diversion bubble line trap line.

Figure 1:
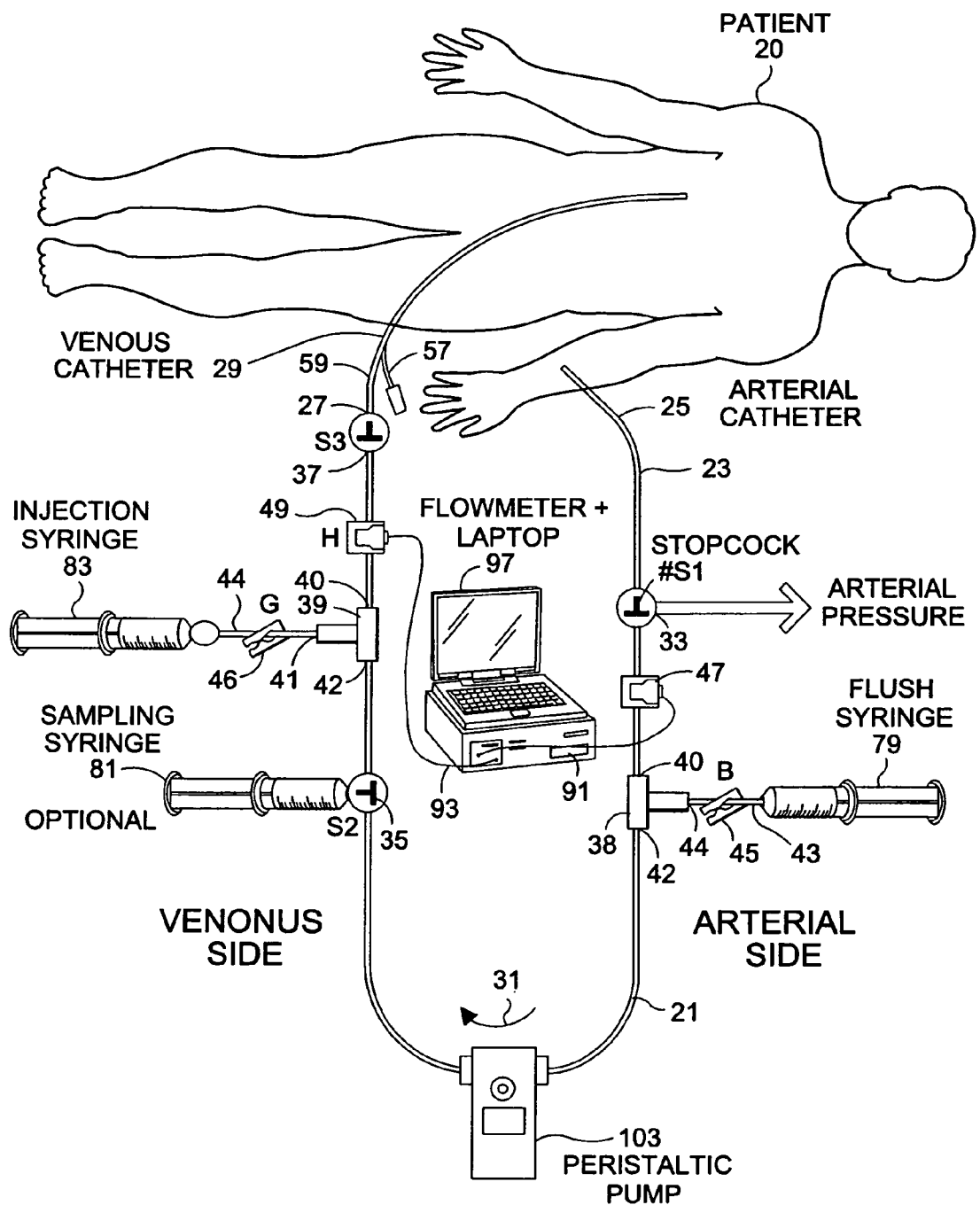
FIG. 1 provides a schematic diagram of one preferred embodiment of the present invention connected to a patient.

A first preferred embodiment of the apparatus of the present invention is depicted in FIG. 1, which provides a schematic diagram of the major components of the system connected to a patient 20. An external blood circulating line or tubing 21 connects at an upstream end 23 to an arterial catheter 25 in patient 20. The down stream end 27 of the circulating line 21 connects to a venous catheter 29 in the patient. Line 21 is standard catheter tubing that creates a fluid connection between the arterial catheter 25 and the venous catheter 29. An arterial catheter 25 is typically placed in a patient in intensive care to periodically monitor the patient's blood pressure. A venous catheter 29 is placed in the patient to provide access for measuring central venous pressure (CVP) and as an intravenous (IV) connection through which prescribed drugs and other medications can be introduced into the patient's blood circulatory system.

Flow of blood in line 21 is in the direction of arrow 31 from the arterial catheter 25 to venous catheter 29. Line 21 also includes standard three way stopcocks 33, 35 and 37 to control flow in line 21 as well as allow for access to line 21 so that samples or portions of blood can be withdrawn or indicators or medication can be introduced.

Access ports 38 and 39 offer additional means for obtaining fluid access to line 21. Access ports 38 and 39 are T type fluid conduit connectors that are open at each end 40, 41 and 42. The conduits inside T's 38 and 39, not shown, that run from each end and share an open interior space. Line 21 makes an unobstructed sealed fluid connection through T 38 and T39 where line 21 connects at end 40 and 42 of each T respectively. Flexible tubes 43 and 44 forms sealed fluid connections to ends 41 respectively of T38 and T39. Tubes 43 and 44 in turn form sealed fluid connections with flush syringe 79 and injection Syringe 83 respectively. Clamps 45 and 46 close off tubes 43 and 44 respectively when access to line 21 is not needed.

Sensors 47 and 49 connect by communication lines 91 and 93 to computer/meter 97. Sensors 47 and 49 are any standard sensor used for indicator dilution measurements. The sensors can be ultrasound sensors, laser sensors, electromagnetic, etc all of which are well known in the art. Each sensor is controlled through signals sent from computer/meter 97 along lines 91 and 93. Signals of reading from sensors 47 and 49 are sent along line 91 and 93 to computer meter 97 for evaluation. Appropriately programmed software, such as HD02 software, running on a standard personal computer with a flow meter alternatively or an HD03 meter, both of which are made by Transonic Systems Inc of Ithaca, N.Y. can be used to control the function of sensors 47 and 49 as well as analyze and display the results of reading taken. The apparatus depicted in FIG. 1 shown a stand Transonic Systems HD02 setup. This specification discuss only two preferred embodiments of transit time ultrasound sensors systems used to measure flow with indicator dilution techniques. Transit time ultrasound sensing for indicator dilution is now well known in the art. However, there are a number of sensor systems or apparatuses that can be used for measurements to determine blood flow which are familiar to those skilled and can be used without departing from the concepts and teachings of the present invention, among them are electromagnetic sensors, laser sensors, or any number of similar types of sensors.

FIG. 2 provides a view of a standard arterial catheter 25, well known in the art, attached to a standard stopcock 33. Arterial catheter 25 has a catheter body 27 that ends in a hub 28 which can be releasably attached to a variety of fluid access control devices, which in FIG. 2 is stopcock 33. Typically, the arterial catheter has only one lumen. A lumen being a fluid conduit passing through the body of the catheter to allow the passage of a liquid. In catheter 25 depicted in FIG. 2 the lumen, which is not shown since it is an interior space in the catheter runs from the exterior end 32 to interior end 30. Catheter body 24 is made of a very flexible and pliable material. Depending on the situation or needs of the patient the arterial catheter can be placed in a central artery or peripheral artery. However, it typically is placed in the radial or femoral artery of the patient. Typically end 30 of catheter 25 does not intrude too far into the artery when placed, only far enough to all the taking of blood pressure.

Referring to FIG. 1, Stopcock 33 controls access between the blood circulating line 21 and the arterial catheter 25. Stopcock 33 is as noted above attached to arterial catheter 25 as a standard procedure to control access to the arterial catheter for obtaining pressure measurements. Referring back to FIG. 2, Stopcock 33 is a standard four way stopcock well known in the art. It has three openings, one 33A that connects to the arterial catheter 25, one 33B through which access can be obtained for making pressure readings and the third opening 33C to which blood line 21 can be attached. Typically a standard stopcock has four settings as follows: 1) all three openings 33A, 33B and 33C are open to each other, 2) access is opened only between opening 33A, and opening 33B, 3) access is only opened between opening 33A and opening 33C and 4) access is only opened between opening 33B and opening 33C. Control lever 36 controls the selection of the four different settings described above. Further discussion regarding the function of this access control device is not necessary since it is well known in the art.

The standard venous catheter 29 FIG. 1 differs in a number of significant aspects from standard arterial catheters. Typically the venous catheter has two lumens or sometimes three lumens. The two lumen catheter will be discussed here and the three lumen catheter will be discussed below. A catheter with at least two lumens is used in the venous catheter set up so that one of the lumens can be dedicated as an intravenous feed (IV) for introducing prescribed medications into the patient etc. The second lumen provides a general access for obtaining central venous pressure (CVP) etc. The venous catheter can be inserted into a central or peripheral vein depending on the circumstances of the patient. However, typically it is inserted into the sub clavicle vein or femoral vein of the patient.

FIG. 3 is a schematic diagram of a two lumen catheter 53. The basic parts of catheter 53 are: 1) the tip 51, 2) distal body 54, 3) catheter body 56, 4) hub 58 and 5) proximal connectors 60. Proximal connectors 60 consist of proximal lumen 57 and distal lumen 59. Proximal lumen 57 and distal lumen 59 join into one body at hub 58. The conduit, not shown, formed by proximal lumen 57 then empties at port 65 at the end of catheter body 56. The conduit formed by distal lumen 59 then continues on and empties at port 67 at tip 51. Typically, proximal lumen 57 is the one through which medication and other substances are fed directly to the patient's circulatory system. Distal lumen 59 allows for access to the patients venous system so the central venous pressure of the patient can be taken. Sections 51, 54 and 56 of catheter 53 are the portions of the catheter inserted into the veins of the patient. Although a short catheter body 56 is depicted in FIG. 3, it can be much longer depending on the application.

Connected to end 69 of lumen 57 is a standard one way valve also known as a check valve 71. In a standard procedure to administer medication intravenously into the patient a syringe could be connected to valve 71 and the medication injected. Alternately lumen 57 could be connected to a continuous intravenous feed with or without valve 71 being present and flow then would be controlled in a standard fashion by side clamp 70.

End 68 of lumen 59 has connected to it a standard four way stopcock 37 an example of which was described above in detail. Stopcock 37 has three openings 74, 75 and 76. Access between the openings is controlled by valve lever 77. This stopcock functions in the same manner as stopcock 33 described above. Three different catheter control devices have been discussed herein 1) stopcocks, 2) one way valves and 3) slide clamp clips. There are other variations of these devices as well as other catheter access control devices all of which are well know in the art and can be used to practice the present invention.

Referring to FIG. 1, flow of blood through lines 21 from arterial catheter 25 to venous catheter 29 is induced and controlled by pump 103. In the preferred embodiment the pump used is a standard peristaltic pump. A peristaltic pump is used because it does not need to come in contact with the blood in line 21.

One of the preferred methods of the present invention includes the following steps: Line 21 such as all of its component parts is assemble but not connected to arterial catheter 25 or venous catheter 29. Stopcock 35 is opened to allow flow along line 21. Line 21 is then filled with a saline solution and then line 21 is connected to arterial catheter 25 and venous catheter 29 as depicted in FIG. 1. Then stopcock 33 and 37 are opened and pump 103 is turned on to start t a flow from end 23 to end 27 of line 21. Once blood flow completely fills line 21 and the original saline in line 21 has dissipated or mixed with the patient's blood, stopcock 35 is set to a position where syringe 81 has fluid access to line 21 and flow downstream in line 21 beyond stopcock 35 is stopped. At the same time slide clamp clip 46 is moved to open up line 44 and thereby allow downstream fluid access for syringe 83 to line 21, upstream flow from line 21 as noted above being blocked.

Syringe 81, which is partially filled with a heparinized saline solution, is set so that it will fill with blood from line 21 to thereby maintain blood flow in line 21 from end 23 to stopcock 35. Simultaneously, syringe 83 which has been filled with an indicator is activated to commence injection of the indicator into line 21 where it then flows downstream into the patient at through lumen 59. Operation of syringe 81 and 83 is coordinated so that syringe 81 accepts blood flowing inline 21 upstream from stopcock 35 while the indicator is injected by syringe 83. Once syringe 83 has completed injection of the indictor. Slide clamp clip 46 is reset closing off of access of syringe 83 to line 21. At the same time stopcock 35 is reset to allow the free flow in line 21 from the upstream direction to the downstream direction with syringe 81, now partially filled with blood, also in fluid communication with line 21. Then the blood in syringe 81 is slowly reintroduced into the blood flow in line 21. When all of the blood from syringe 81 has been reintroduced into line 21 stopcock 35 is reset again to close off syringe 81 from line 21 but allow the continued flow of blood through line 21 from end 23 to end 27. Readings are taken with one or both sensors 47 and 49 at the appropriate time to determine the concentration of indicator in the blood circulating through line 21.

Figure 4:
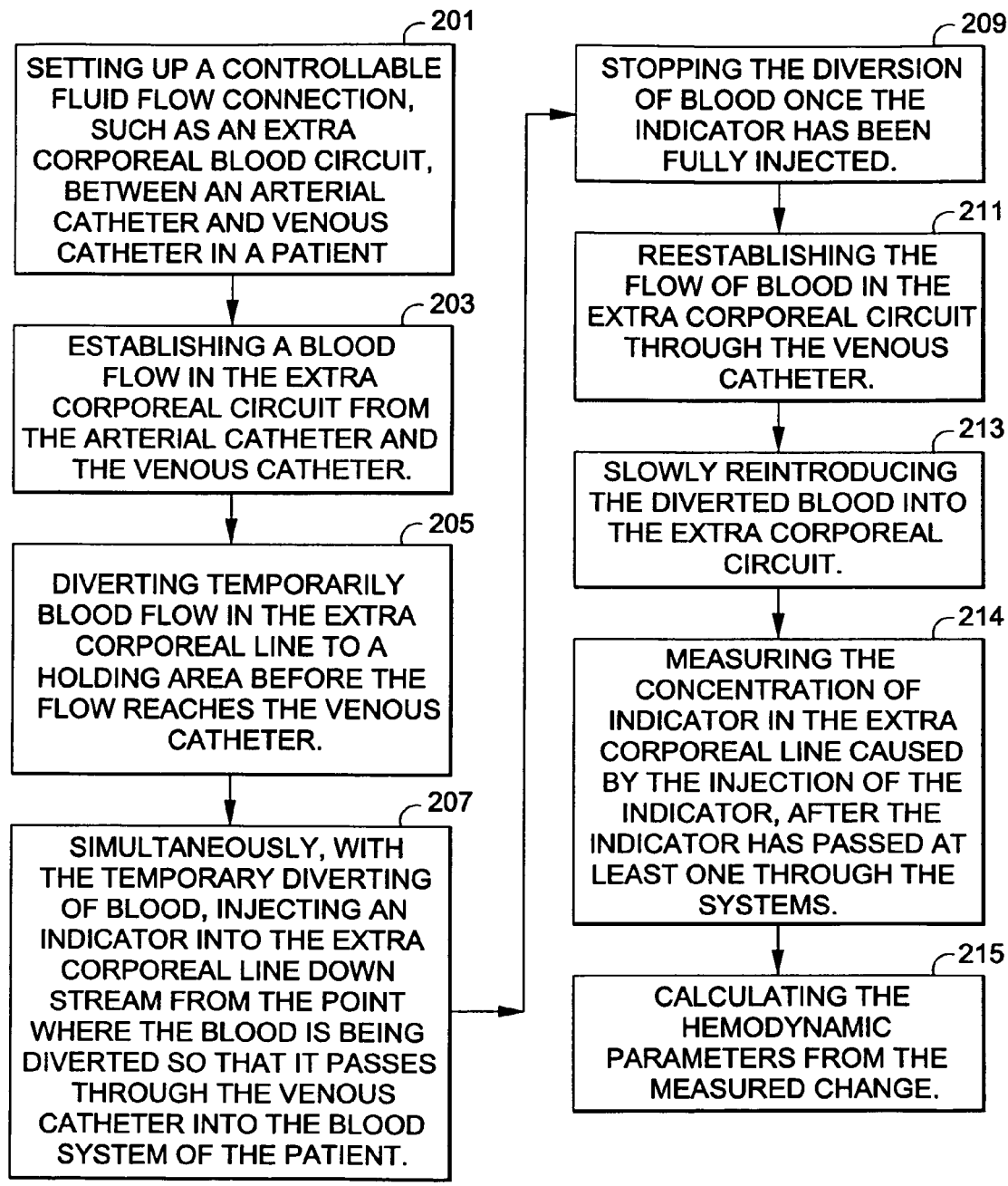
FIG. 4 is a flow chart of one variation of a method of the preferred embodiment of the present invention.

Thus as depicted in the flow chart of FIG. 4 the method of the present invention consists of setting up a controllable fluid connection, such as the extracorporeal blood circuit depicted in FIG. 1, between an arterial catheter and venous catheter in a patient 201. Establishing a blood flow in the extracorporeal circuit from the arterial catheter to the venous catheter 203. Diverting temporarily blood flow in the extracorporeal line to a holding area before the flow reaches the venous catheter 205. Simultaneously, with or shortly after commencing the temporary diverting of blood, injecting an indicator into the extracorporeal line down stream from the point where the blood is being diverted so that it passes through the venous catheter into the circulatory system of the patient 207. Once the indicator has been fully injected stopping the diversion of blood 209. Reestablishing the flow of blood in the extracorporeal circuit through the venous catheter 211. Slowly reintroducing the diverted blood into the extracorporeal circuit 213. Measuring the concentration of indicator in the extracorporeal line caused by the injection of the indicator 215. Calculating the hemodynamic parameters from the measured change 217.

Figure 5:
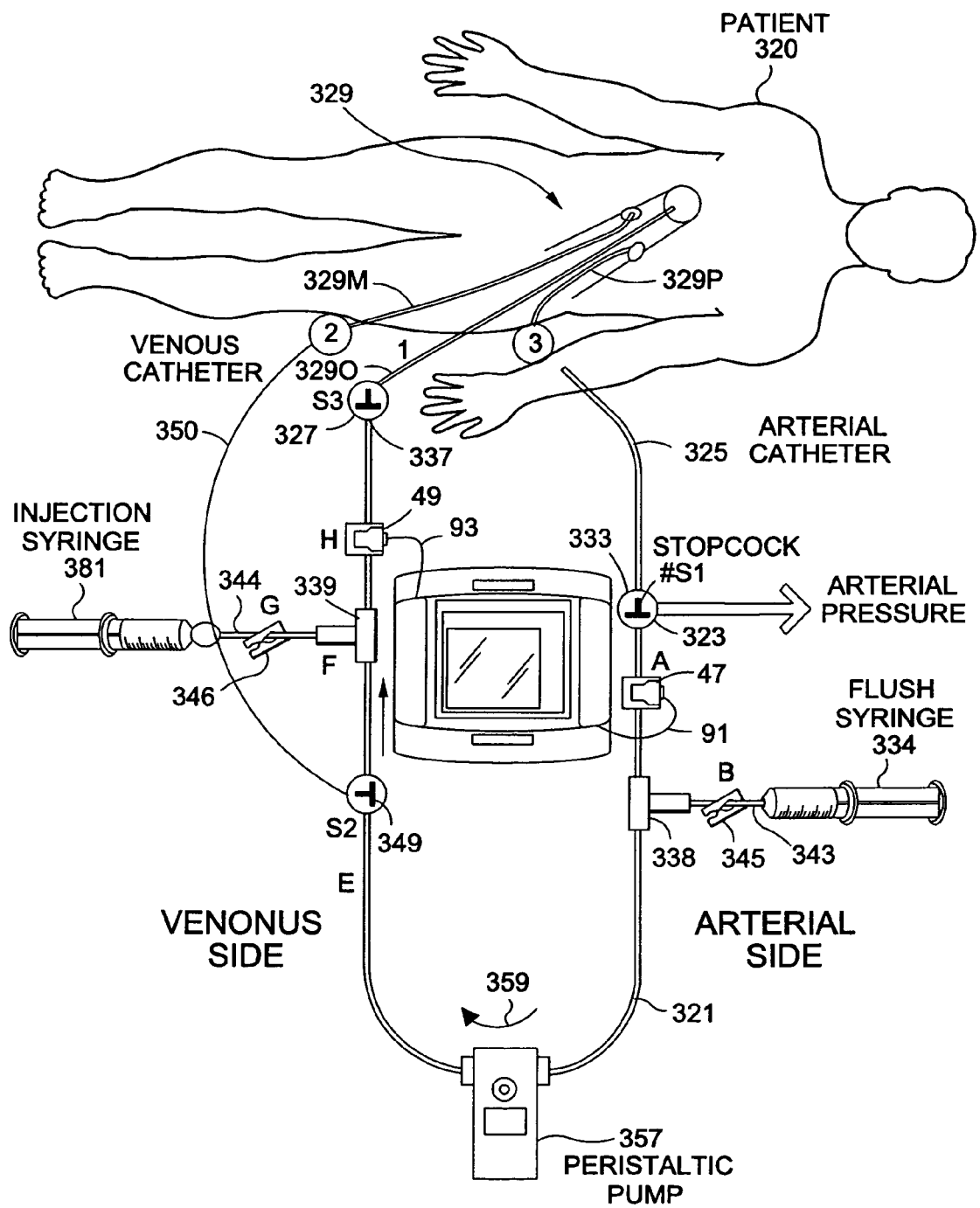
FIG. 5 provides a schematic diagram of another preferred embodiment of the present invention.

FIG. 5. provides a schematic diagram of another preferred embodiment of the present invention and its connection to a patient 20. In FIG. 5. blood line 321 at an upstream end 323 connects to arterial catheter 325 through stopcock 333. External blood line 321 connects at a downstream end 327 to one of the lumens 329D of triple lumen catheter 329 though stopcock 337. Line 321 includes standard liquid conduit T connectors 338 on the arterial side and 339 on the venous side to allow access for flush syringe 334 and injection syringe 381 respectively.

Injection syringe 381 connects to liquid conduit T connector 339 though tubing 344. Slide clamp clip 346 controls the opening of tube 344 to allow the passage of a liquid between line 321 and injection syringe 381. Likewise slide clamp clip 345 controls the opening of the tube 343 to allow the passage of liquid between flush syringe 334 and line 321. Tube 343 connects to both T 338 and flush syringe 334.

In this variation of the invention stopcock 349 in line 321 provides an operable fluid connection to tube 350, which tubing in turn is connected to the $2^{nd}$ or medial lumen 329M of the three lumen catheter 329. The third lumen 329P, the proximal lumen of the three lumen catheter 329 is used to administer medication by an intravenous feed that is not shown.

In this variation of the invention sensors 47 and 49 connect respectively by lines 91 and 93 to a Transonic HD03 Flowmeter. The HD03 being an upgrade of Transonic Systems Inc of Ithaca N.Y., HD02 system previously mentioned. As previous noted this is one of the preferred embodiments of the present invention, but there are many other sensor arrays known by those skilled in the art that can be used to take the readings and analyze the data and not depart from the concepts and spirit of the present invention. The ultimate objective of the sensors and flow meter being the determination of indicator concentration in the blood after it circulates through patient 20's circulatory system. From this information cardiac output and other hemodynamic parameters are determined.

Figure 6:
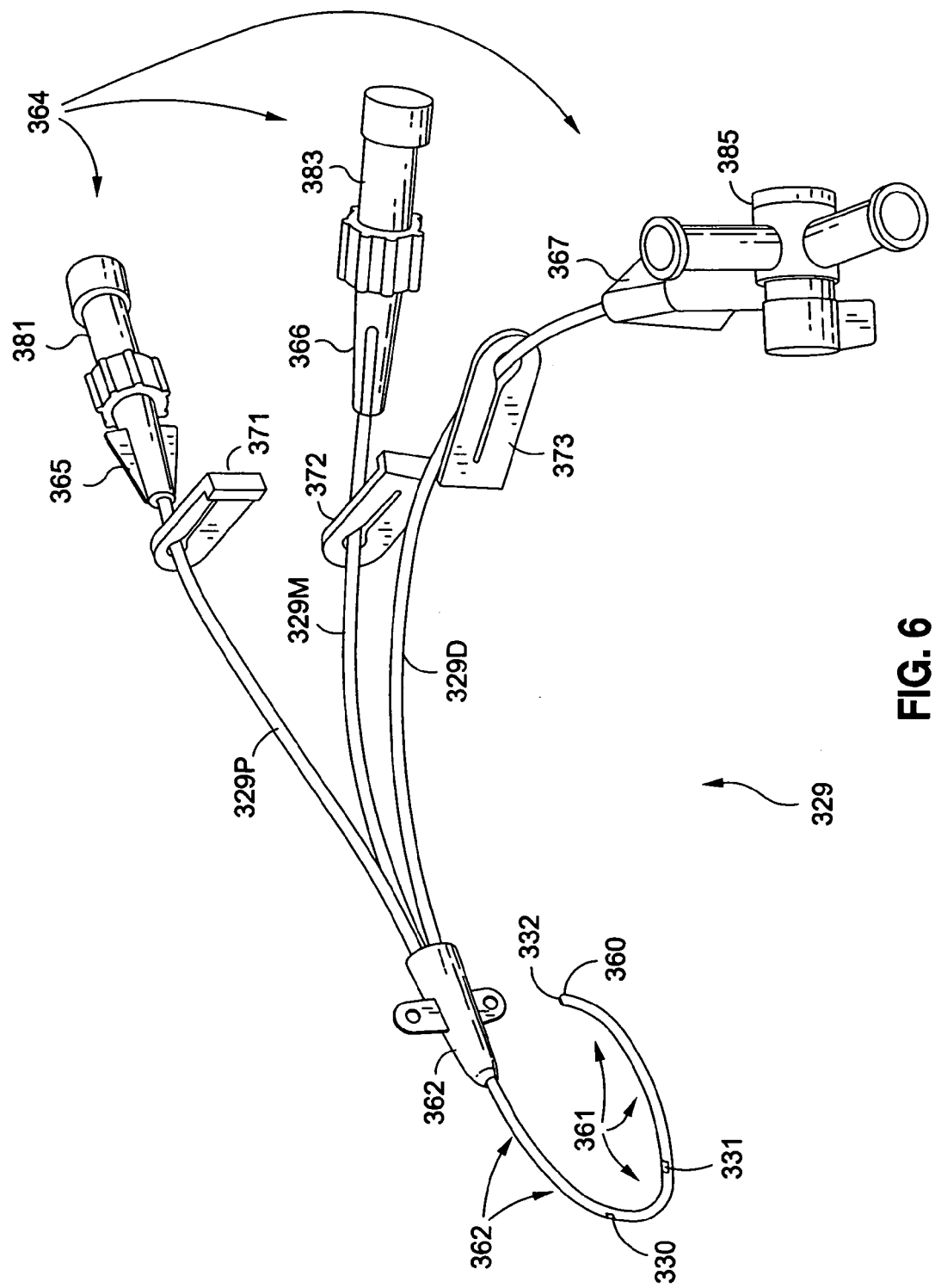
FIG. 6 is a view of a three lumen venous catheter with which another preferred embodiment of the present invention might be practiced.
Figure 7:
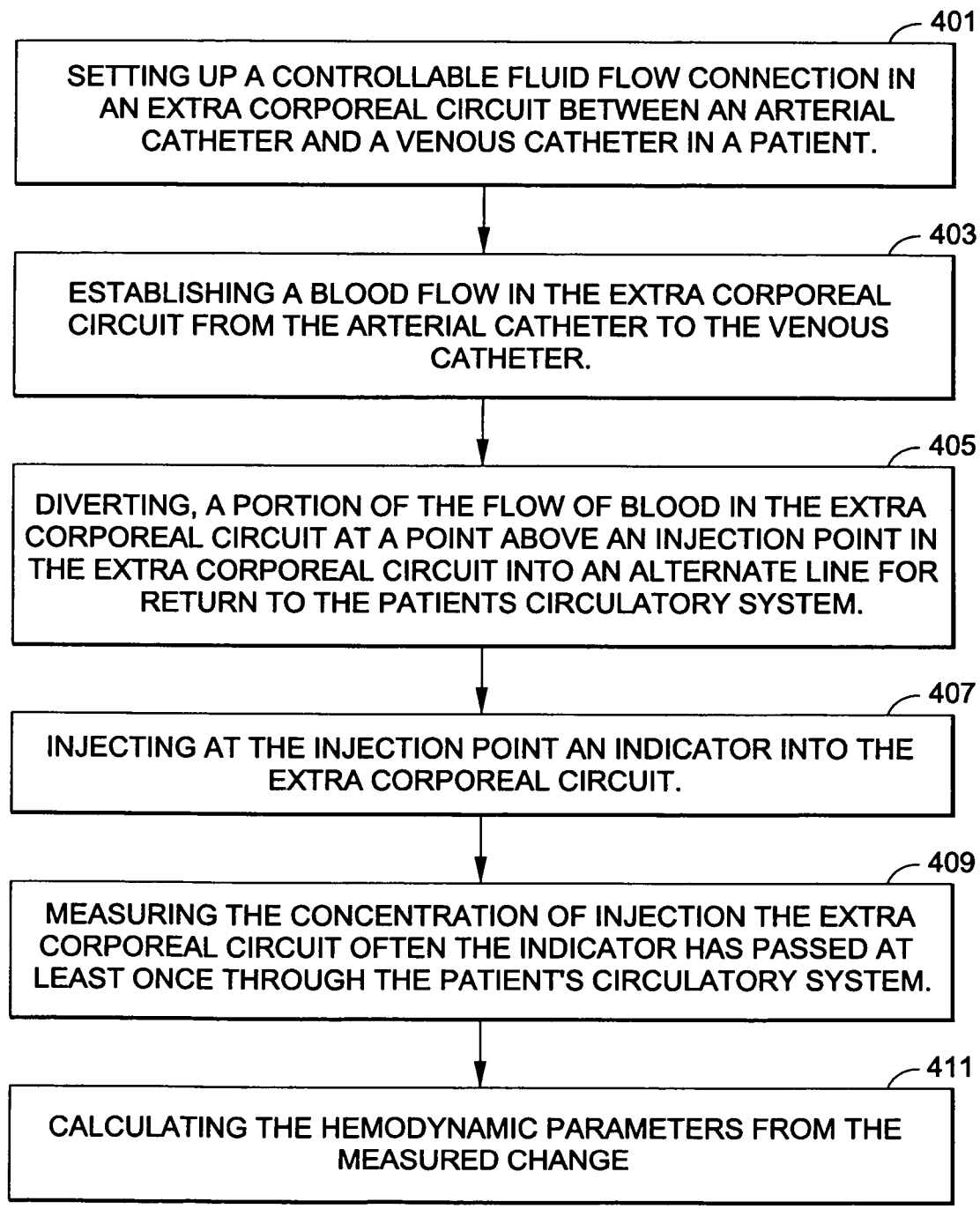
FIG. 7 is a flow chart of another variation of the method of the present invention.

FIG. 6 provides a perspective view of one variation of a three lumen catheter 329 that might be used with the present invention. Three lumen catheter 329 has a tip 360, a distal end 361, a catheter body 362, a hub 363 and proximal connectors 364. Proximal connectors 364 consist of proximal lumen 329P, medial lumen 329M and distal lumen 329D. Each lumen forms a separate conduit. All three lumens 329P, 329M and 329D are joined together at hub 363. The conduits formed by each lumen then pass through catheter body 362. The conduit formed by proximal lumen 329P ends at interior port 330 at the beginning the distal end 361. The conduit formed by medial lumen 329M passes into distal end 361 and has an opening at interior medial port 331. The conduit formed by distal lumen 329D passes through distal end 361 and has an opening interior distal port 332 at tip 360.

As is well know in the art each of the conduits formed by each lumen is separate from the other. Since the conduits are inside the structure of the catheter they are not shown. The conduit formed by proximal lumen 329P has an exterior opening, not shown at the end of fastener 365, which forms the end of proximal lumen 329P. The conduit formed by proximal lumen 329P runs from interior port 330 to the exterior opening in fastener 365, and thus allows fluid communication between the interior port and exterior opening. Likewise, the conduit formed by medial lumen 329M has an exterior opening not shown on fastener 366, which fastener forms the end of medial lumen 329M. This conduit then runs from exterior opening at the end of fastener 360 to interior port 331 to allow fluid communication between the exterior opening and interior port 331. Finally, the conduit formed by distal lumen 329D runs from the exterior opening formed by fastener 367, which fastener forms the end of distal lumen 329D, to interior port 332 to allow for fluid communication between these points.

The hub 363 and fastener 365, 366 and 367 are generally made of a hard plastic type of material. On the other hand lumens 329P, 329M and 329D as well as catheter body 362, distal end 361 and tip 360 are all made of a very flexible and pliable material. Catheter body 362, distal 361 and tip 360 are the portion of the catheter that is inserted into the veins of the patient.

There are various ways to control access and flow in each lumen of catheter 329. Some of these ways to control access and flow were discussed above in some detail and will be mentioned again. One way valves 381 and 363 are each detachably connected to fasteners 365 and 366 respectively. The ones shown have screw on attachments not shown. Stopcock 385 is attached to fastener 367 by a twist mechanism not shown. Additionally, each lumen has a slide clamp clip 371, 372 and 373 to provide an additional means for controlling access and flow.

A somewhat detailed discussion with descriptions have been provided regarding arterial catheters, two lumen venous catheter and a three lumen venous catheter. This has been included to provide a basis for discussing the preferred embodiments of the present invention. All of the information concerning catheters, their structure and function is well known in the art. Thus, what has been detailed is by way of example and not meant to limit in any way the invention. There are other types of catheters and similar devices well known in the art which could just as easily be used without departing from teaching of the present invention.

The method of this preferred embodiment of the present invention includes assembling line 321 as depicted in FIG. 5 connecting it to stopcocks 337 and 333. When line 321 is connected to stopcock 333 and 337 they are in the closed position so there is no fluid communication between catheter 325 catheter 329 and line 321. Flush syringe 334 has been filled with a heparinized saline solution. Clamp 345 is released and the saline solution in syringe 334 is injected into line 321 to fill it. Flow is then started in line 321 by opening stopcocks 333 and 337 and starting pump 357. Once blood completely fills line 321 stopcock 349 is also opened to allow blood flow in line 350 to lumen 329M and then back into the patient's circulatory system. It should be noted at all times tub 350 and lumens 329M and 329D are all pre-primed with saline solution to avoid the introduction of air into the patient's circulatory system.

Next clamp 346 is released to open fluid communication between injection syringe 381 and line 321. The indicator injection syringe then injects the indicator it contains into line 321. Since part of the blood flow in line 321 is being diverted above T 329 back to the patient by way of line 350 and medial lumen 329M, flow volume is decreased in line 321 at stopcock 349 through distal lumen 329D to the patient. This decreased flow volume allows the easy injection of indicator in syringe 381 into the patient without an excessive spike in pressure or the reversal of flow in line 321.

Thus, the steps of this preferred embodiment of the present invention consists of: setting up a controllable fluid flow connection in an extracorporeal circuit between an arterial catheter and a venous catheter in a patient 401. Establishing a blood flow in the extracorporeal circuit from the arterial catheter to the venous catheter 403. Diverting, a portion of the flow of blood in the extracorporeal circuit at a point above an injection point in the extracorporeal circuit into an alternate line for return to the patients circulatory system 405. Injecting at the injection point an indicator into the extracorporeal circuit 407. Measuring the concentration of injection the extracorporeal circuit after the indicator has passed at least once through the patient's circulatory system 409. Calculating the hemodynamic parameters from the measured change 411.

The two preferred embodiments described above require operator intervention to first commence the accumulation of diverted blood from the extracorporeal circuit while the indicator is being injected and then reintroducing the diverted blood in the case of the first embodiment or shutting off of the diversion route in the case of the second example. Two addition preferred embodiments will now be described that provide an automatic set up that accumulates or diverts that flow of blood during the injection process and then automatically reverses the process once the injection of the indicator ceases. Both of the preferred methods or systems described below use a one way or check value to prevent reverse flow and eliminate the need to use stop cocks.

Figure 8:
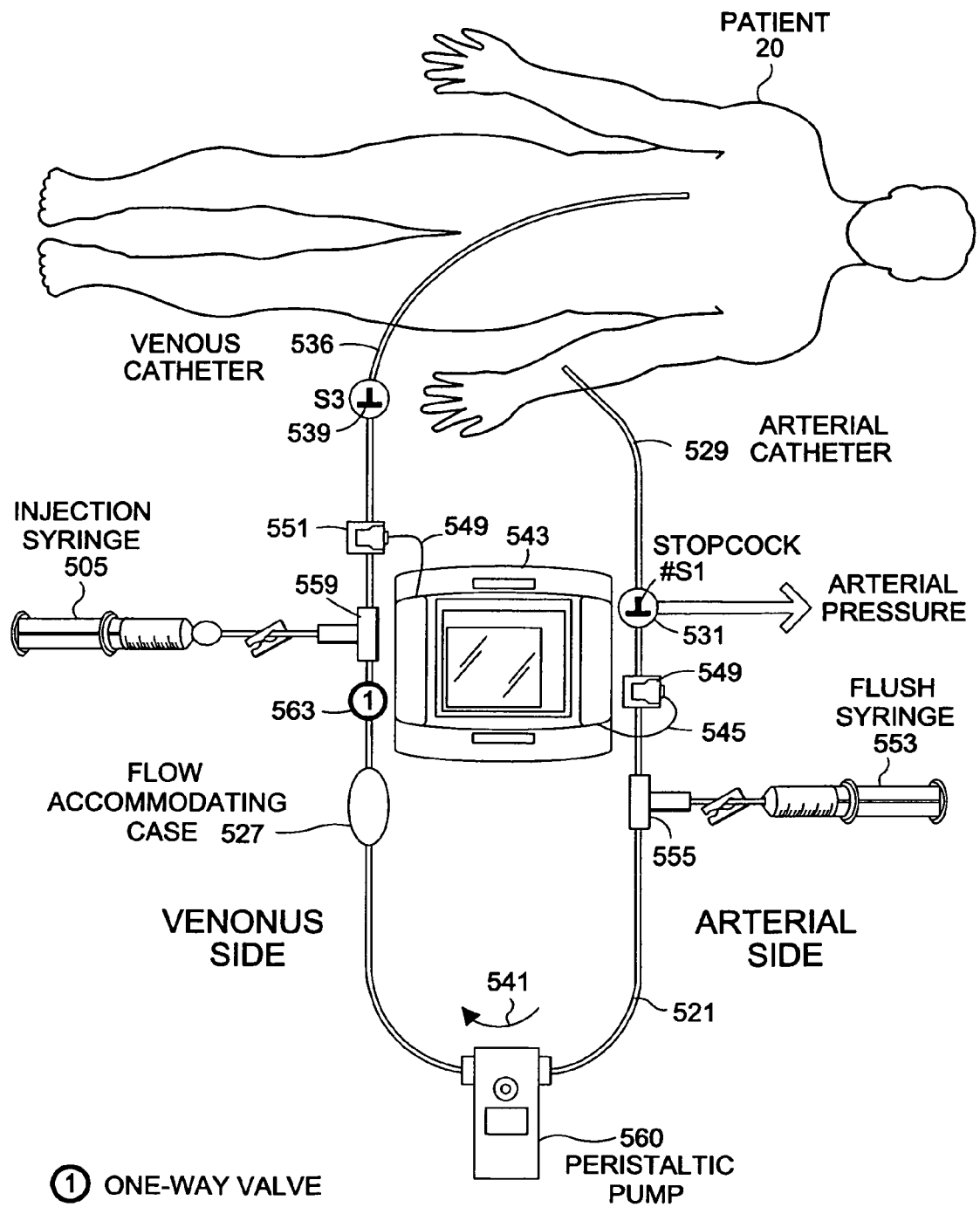
FIG. 8 provides schematic diagrams of another preferred embodiment of the system of the present invention attached to a patient that uses a volume accumulating case that expands as blood flow is interrupted during injection then releases the accumulated blood as flow is reestablished.

FIG. 8 is a schematic diagram of a set up of a system that would use another preferred embodiment of the present invention that provides for the automatic release of blood that has accumulated during injection of the indicator. During the injection of indicator by injection syringe 505 the pressure of forcing the indicator into circulatory line 521 causes the blood circulating in line 521 to back up and accumulate in flow accommodating case 527, which as described in detail below expands to accommodate the blood displaced during injection of the indicator. In most other respects the set up depicted in FIG. 8 is the same or similar to those in FIGS. 1 and 5. In FIG. 8 circulating line 521 connects to arterial catheter 529 at stop cock 531 and venous catheter 536 at stop cock 539. Blood flow in circulating line 521 flows in the direction of arrow 541. Computer flow meter 543 connects through line 545 to sensor 549 and line 547 to sensor 551. Flush syringe 553 connects to circulating line 521 through T connector 555. Injection syringe 505 connects to circulating line 521 through T connector 559. Peristaltic pump 560 controls flow as described above.

A one way valve or check valve 563 on line 521 prevents injected indicator from injection syringe 505 or blood that has flowed past check valve 563 from being forced back upstream in circulating line 521. However, when injection syringe is injecting indicator into line 521 check valve 563 will in all probability be forced closed blocking, during the injection process, the flow of blood in line 521 above valve 563. When flow is thus blocked this does not interrupt flow in the rest of circulating line 521 since flow accommodating case 527 expands to accommodate the blood that is blocked from flowing past check valve 563, thus case 527 acts as an expanding reservoir or volume accumulating chamber. Once the injection of indicator by injection syringe 505 has ended check valve 563 reopens and the flow in line 521 is reestablished from check valve 563 to venous catheter 536 and the excess blood accumulated in flow accommodations case 527 flows out. Thus, when the injection of indicator starts in this embodiment flow is stopped and accumulates and once the injection is completed flow recommences and the accumulated blood automatically flows through the system to venous catheter 536.

Figure 9:
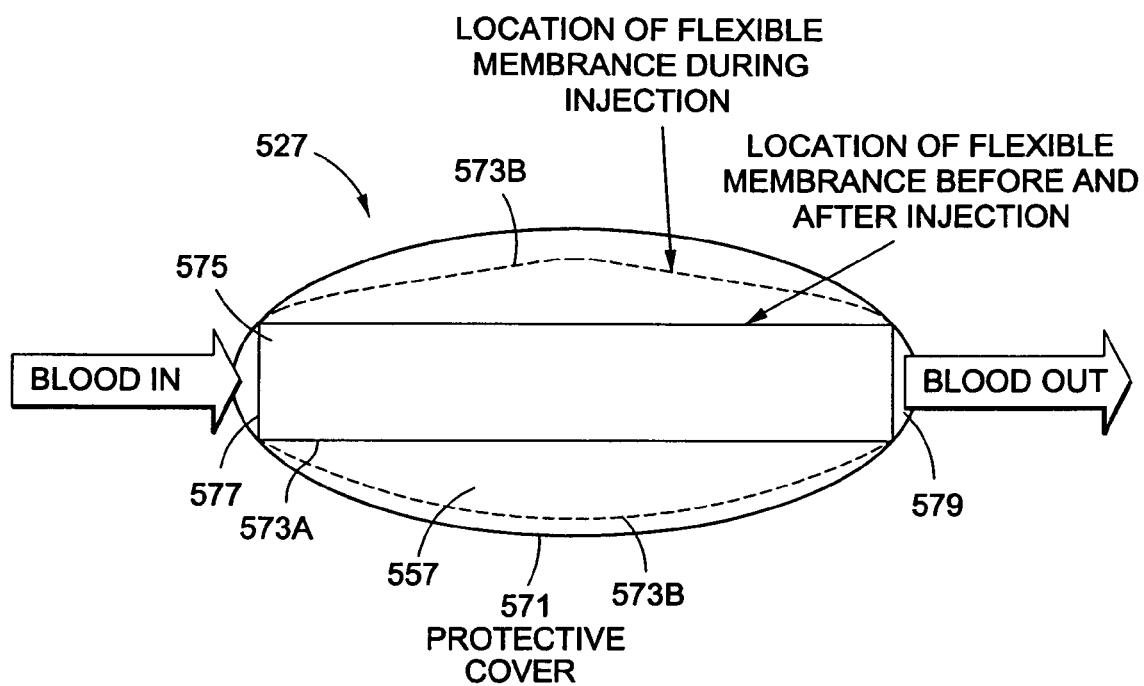
FIG. 9 provides a view of the volume accumulating case, of the embodiment depicted in FIG. 8, that expands to accumulate blood when flow is interrupted and then releases the accumulated blood after flow is restored in the system at the end of the injection of indicator.

FIG. 9 provides a schematic diagram of one variation of flow accommodating case 563. It consist of a rigid outer shell 571 with an expandable conduit 573 which before an injection forms flow channel 575 through case 571 with a diameter approximately equal to the diameter of circulating line 521. Blood flows through channel 575 from entrance 577 to exit 579. However, when flow is interrupted by an injection conduit 573 expands from position 573A to 573B to accommodate the build up of blood caused by the interruption of flow. Once the injection stops and flow is no longer interrupted 573 conduit contracts from its expanded position at 573B back to its position during normal flow 573B. Conduit 573 can be made of any suitable flexible rubber like material.

The size that the interior space 557 of expansion chamber 527 into which expanding conduit 573 will need to expand can be easily determined by calculating the amount of blood that would accumulate during injection of the indicator. In making the calculation one would start with the pump rate at which the pump will continue to pump blood. For example if the pump rate is 12 ml/min (0.2 ml/sec) and the injection typically lasts for 6 seconds then the volume that would be accumulated by the flexible membrane of conduit 573 is 0.2 ml×6=1.2 ml. As noted above, after the injection is finished one-way or check valve 563 will reopened and the extra volume of blood accumulated in the flexible membrane of conduit 573 will be released into the system. Naturally, it is important that the membrane has sufficient flexibility to accommodate the estimated volume of blood that will accumulate.

Figure 10A:
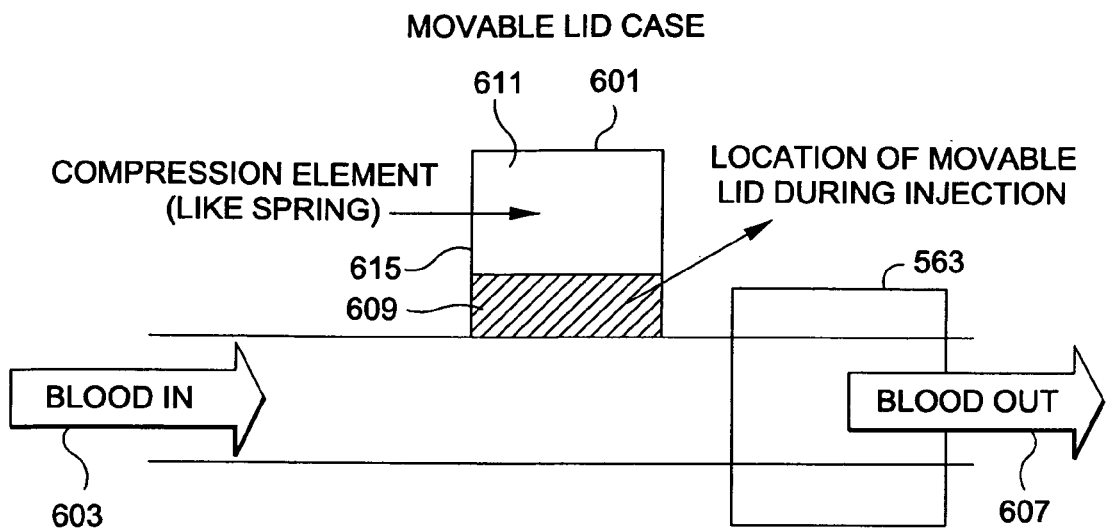
FIG. 10A provides a schematic diagram of yet another embodiment that uses and expanding chamber in the system of FIG. 8 to accommodate accumulating blood when flow of blood is interrupted during the injection process by a shut off valve, the view in FIG. 10A being of the chamber before pressure of the accumulating blood forces the chamber to open to accumulate blood.
Figure 10B:
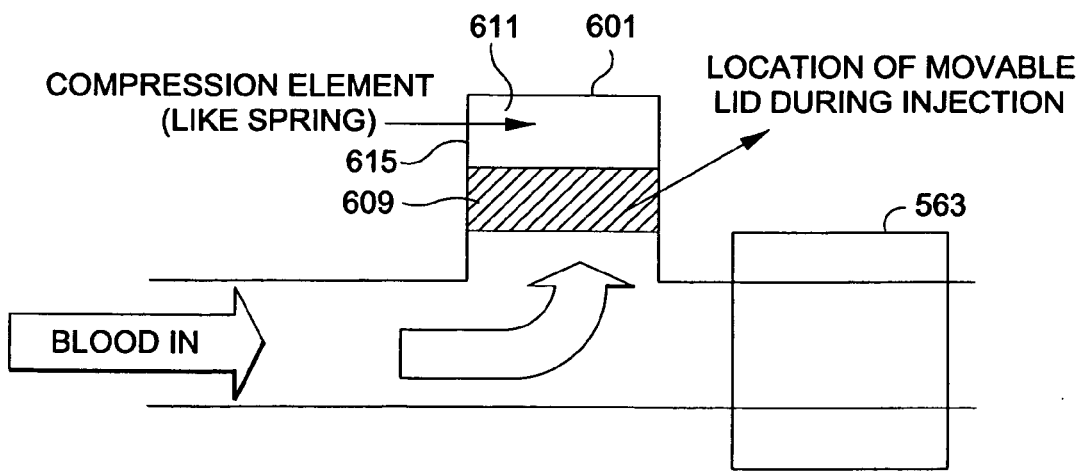
FIG. 10B provides a view of the expansion chamber of 10B when the accumulating blood forces the chamber to open and accumulate blood and then contract releasing the accumulated blood when flow is restored.

FIGS. 10A and 10B provide a schematic view of another variation of a volume accommodating chamber or expansion reservoir 601 for accumulating blood during an injection with syringe 505 (FIG. 8). Referring to FIG. 10A when check valve 563 is open normal unobstructed flow along line 521 occurs as indicated with blood flow as indicated by arrows 605 and 607. Expansion chamber 601 has a lid 609 and a compression element 611 behind it. Lid 609 naturally has a tight seal with the sides of expansion chamber 601. Compression element 611 can be a spring or similar type of device that responds to pressure by compressing but returns to an expanded position when the excess pressure is removed. Referring to FIG. 8 when an injection with syringe 505 begins the injectate displaces the blood flowing in line 521, this causes blood upstream from the injections site to back up and force check valve 563 closed. Referring to FIG. 10B once check valve 563 closes as a result of the injection, blood begins to accumulate upstream from check valve 563 causing pressure to build up to the point where the accumulating blood forces lid 609 to compress spring or compression element 611. The movement of lid 609 into expansion chamber 601 creates an expanding reservoir in which the blood flowing upstream from check valve 563 accumulates. Once the injection ceases and check valve 563 reopens the pressure causing compression element 61 to collapse, the force of the accumulating blood, is withdrawn compression element 611 will then force lid 609 back to its first position in FIG. 10A. This naturally reintroduces the diverted blood back into line 521.

Thus as is readily apparent both the preferred embodiments shown in FIGS. 8, 9, 10A and 10B are in effect automatic systems which by means of mechanical methods provide systems to automatically accumulate blood when the flow of blood needs to be diverted during an injection and then automatically reintroduce the accumulated blood back into the system without further human intervention. One way or check valves 563 are well known in the art. The description of Flow accommodating Case 527 and flexible conduit 573 or movable lid case 601 or its component parts the above description should be sufficient for those of ordinary skill in the art to make and use them.

Figure 11:
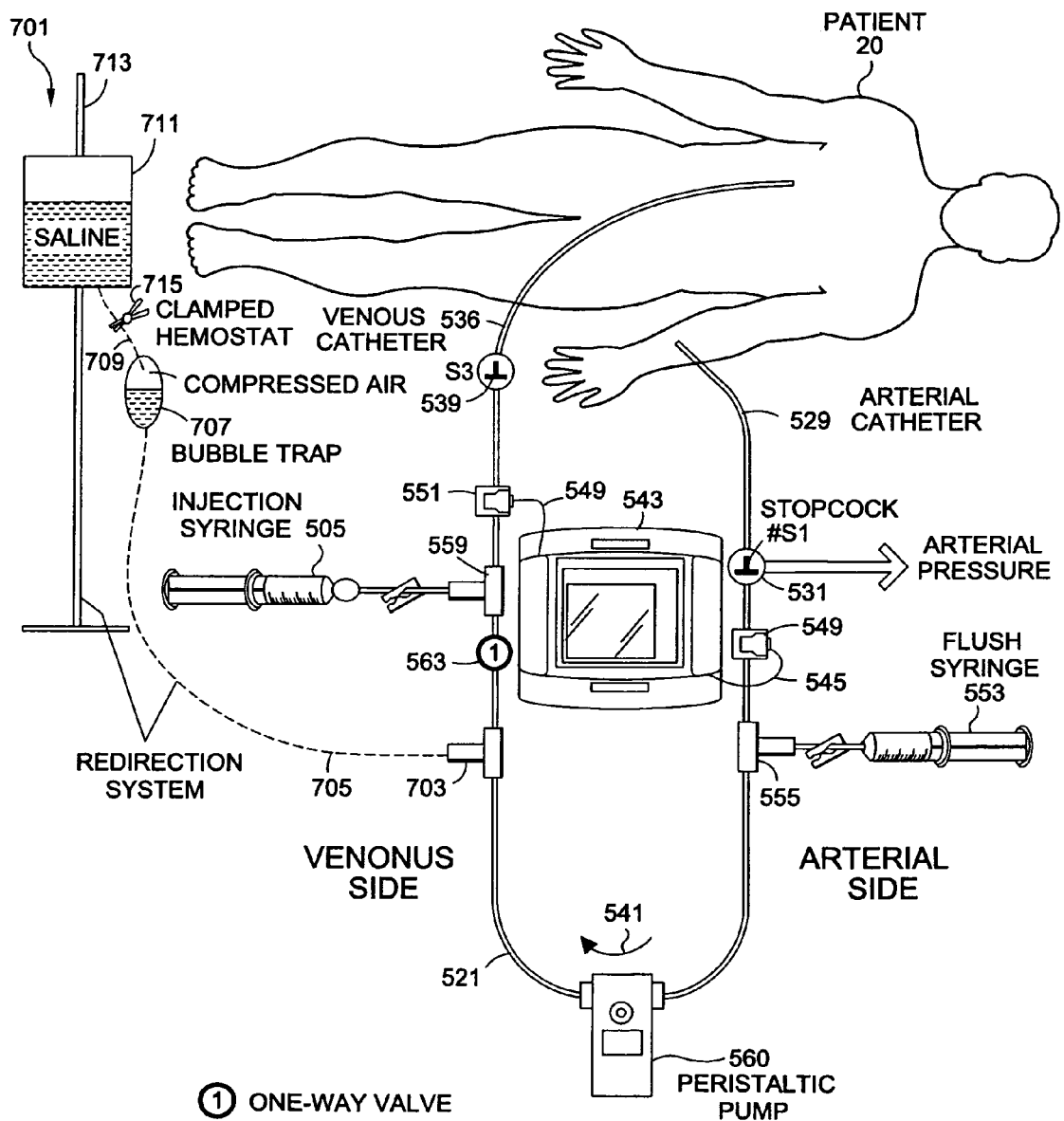
FIG. 11 is a detailed schematic view of another system that automatically diverts blood during and injection to a bubble trap line and then returns it to the system.

FIG. 11 is a schematic diagram of another system and method for automatically diverting blood flow during and injection. The automatic flow diversion system depicted in FIG. 11 is the same in all respects as that in FIG. 8, with one exception flow accommodating case 527 is not used and is replaced with an automatic flow pressure relief system 701. Otherwise all of the other features of the system depicted in FIG. 11 are the same as those depicted in FIG. 8 and have the same identifying numbers.

Automatic flow pressure relief system 701 consists of T connector 703 fluid line 705, bubble trap 707, fluid tubing 709, saline bag 711, stand 713 and tubing clamp 715. In system 701 T connector 703 puts a first end of fluid tubing line 705 in fluid contact with blood circulating line 521 at a position upstream from check valve 563 and downstream from pump 560. At a second end fluid tubing line 705 is in fluid communication with bubble trap 707 and bubble trap 707 is in fluid communication with saline filed bag 711 through fluid line 709. Saline bag 711 is connected to stand 713 at a point above the plane of the patient 20 so that when saline fluid is released from bag 711 by removal of clamp 715 it flows down into bubble chamber 707 which is below saline bag 711 and on into tubing 705 which is below bubble trap 707.

In typical setup when automatic flow pressure system is first assembled, before the introduction of saline fluid, and the first end of fluid tubing line 705 is connected to T 703 clamp 715 is removed and enough saline liquid is allowed to flow into bubble trap 707 and line 705 to completely fill line 705 and half file bubble trap 707. Once bubble trap 707 is half full flow of fluid from saline bag 711 is stopped by reconnecting clamp 715 to line 709. As is typical with this type of set up when blood is flowing in line 521 under pressure created by the action of pump 560 a fluid pressure balance is reached between blood flowing in line 521 and saline solution line 705 of system 701 so that saline fluid is not forced and does not flow into line 521. However, when injection syringe 505 injects an indicator into line 521 one way valve 563 closes, then pressure builds up above valve 563 as the result of accumulating blood. This build up of pressure causes blood to be diverted into line 705 and fluid in line 705 then backs up into bubble trap 707.

Once the injection is finished and valve 563 reopens the build up of pressure is relieved and the blood that has flown into line 705 begins to flow back into line 521 until it has all flown back out of line 705. At this point the pressure balance between automatic flow pressure relief system 701 and blood line 521 are back in their original pressure balance and more fluid does not flow into line 521. It should be noted that this system works by compressing the air in the bubble chamber 707 and against the force of gravity when blood is forced into line 705 during injection of the indicator. Another variation of this invention could dispense with the saline bag and have a sealed partially filed chamber in fluid communication with line 705.

Although the present invention has been described in terms of preferred embodiments, it will be understood that variations and modifications may be made without departing from the true spirit and scope thereof.

We claim:

1. A system for facilitating the determination of hemodynamic parameters in a patient comprising:
 a. an extracorporeal circuit with a first end that connects to an arterial catheter of a patient and a second end connecting to a venous catheter of the patient;
 b. a fluid propelling apparatus to draw blood into the extracorporeal circuit from the first end;
 c. at least one injection port on the extracorporeal circuit for fluid access to the extracorporeal circuit;
 d. a dilution indicator bolus injector fluidly connected to the at least one injection port;
 e. a volume of dilution indicator in the dilution indicator bolus injector; and
 f. a flow volume accommodating case for diverting blood in the extracorporeal circuit while (i) the volume of the dilution indicator is being injected into the extracorporeal circuit at the at least one injection port (ii) blood is drawn into the extracorporeal circuit and (iii) an open flow path is maintained from the at least one injection port to the venous catheter, whereby the flow accommodating case includes a resilient member that will automatically expand and contract in response to pressure from the open flow path enabling pressure to be relieved from the open flow path.

2. A system for facilitating the determination of hemodynamic parameters comprising:
 a. an extracorporeal circuit with a first end that connects to an arterial catheter of a patient and a second end that connects to a venous catheter of the patient;
 b. a fluid propelling apparatus to move fluid into the extracorporeal circuit through the first end;
 c. at least one injection port on the extracorporeal circuit;
 d. a dilution indicator bolus injector fluidly connected to the at least one injection port;
 e. a volume of dilution indicator in the dilution indicator bolus injector; and
 f. a flow volume accommodating case including a resilient member that will automatically expand and contract enabling pressure relief and is in fluid communication with the extracorporeal fluid circuit at a position upstream on the extracorporeal circuit from the at least one injection port, the flow accommodating case (i) receiving accumulating fluid resulting from a constriction or interruption of flow downstream by the dilution indicator passing from the dilution indicator bolus injector into the extracorporeal circuit and (ii) releasing the accumulated fluid to flow into the extracorporeal circuit when the constriction or interruption of flow ceases, the flow accommodating case receiving accumulating fluid occurring during unrestricted flow from the at least one injection port to the second end.

3. The system of claim 1, wherein the flow volume accommodating case is fluidly intermediate the first end and the at least one injection port.

4. The system of claim 1, wherein the flow volume accommodating is upstream of the at least one injection port.

5. The system of claim 1, further comprising a one way check valve fluidly intermediate the at least one injection port and the flow volume accommodating case.

6. The system of claim 1, further comprising a one way check valve fluidly intermediate the at least one injection port and the first end.

7. The system of claim 1, wherein the flow volume accommodating case automatically returns blood to the extracorporeal fluid conducting circuit.

8. The system of claim 2, wherein the flow volume accommodating case is fluidly intermediate the first end and the at least one injection port.

9. The system of claim 2, wherein the flow volume accommodating case is upstream of the at least one injection port.

10. The system of claim 2, further comprising a one way check valve fluidly intermediate the at least one injection port and the flow volume accommodating case.

11. The system of claim 2, further comprising a one way check valve fluidly intermediate the at least one injection port and the first end.

12. The system of claim 2, wherein the flow volume accommodating case automatically returns blood to the extracorporeal fluid conducting circuit.

13. The system of claim 1, wherein the flow volume accommodating case during injection and returning the diverted blood after injection includes a diverting lumen providing an alternate route back to said venous catheter.

14. The system of claim 1, wherein the flow volume accommodating case during injection of the dilution indicator and returning the diverted blood after injection of the dilution indicator includes a syringe connected to said extracorporeal circuit for manually diverting blood.

15. The system of claim 1, wherein (i) the dilution indicator is being injected into the extracorporeal circuit at the at least one injection port, (ii) the blood is drawn into the extracorporeal circuit and (iii) the flow path is maintained open from the at least one injection port to the venous catheter at the same time.

16. A system for facilitating the determination of hemodynamic parameters comprising:
   a. an extracorporeal circuit having a first end that connects to an arterial catheter of a patient and a second end that connects to a venous catheter of the patient;
   b. a pump to move fluid into the extracorporeal circuit from the first end;
   c. at least one injection port on the extracorporeal circuit;
   d. a dilution indicator bolus injector fluidly connected to the at least one injection port;
   e. a volume of dilution indicator in the dilution indicator bolus injector; and
   f. a flow volume accommodating case including a resilient member that will automatically expand and contract to enable pressure relief and in fluid communication with the extracorporeal fluid circuit at a position upstream on the extracorporeal circuit from the at least one injection site for receiving accumulating fluid resulting from a pressure spike in the flow downstream caused by the dilution indicator bolus passing from the dilution indicator bolus injector into the extracorporeal circuit while maintaining an open flow path between the injection port and the second end.

* * * * *